(12) United States Patent
Matsuyama

(10) Patent No.: US 7,686,674 B2
(45) Date of Patent: Mar. 30, 2010

(54) CUP ATTACHING APPARATUS

(75) Inventor: Yoshinori Matsuyama, Anjo (JP)

(73) Assignee: Nidek Co., Ltd., Gamagori-shi (JP)

( * ) Notice: Subject to any disclaimer, the term of this patent is extended or adjusted under 35 U.S.C. 154(b) by 330 days.

(21) Appl. No.: 11/730,158

(22) Filed: Mar. 29, 2007

(65) Prior Publication Data
US 2007/0232194 A1 Oct. 4, 2007

(30) Foreign Application Priority Data
Apr. 3, 2006 (JP) .............................. 2006-101444

(51) Int. Cl.
  *B24B 13/00* (2006.01)
(52) U.S. Cl. .............................. 451/6; 451/42; 451/460
(58) Field of Classification Search .................... 451/42, 451/6, 5, 384, 390, 460
See application file for complete search history.

(56) References Cited

U.S. PATENT DOCUMENTS

| | | | | |
|---|---|---|---|---|
| 1,727,889 | A * | 9/1929 | McCabe ..................... | 451/460 |
| 3,451,177 | A * | 6/1969 | Buckminster et al. ....... | 451/460 |
| 3,710,849 | A | 1/1973 | Hines et al. | |
| 3,858,982 | A | 1/1975 | Meckler | |
| 5,498,200 | A * | 3/1996 | Werner ........................ | 451/460 |
| 5,720,647 | A | 2/1998 | Gottschald | |
| 6,056,633 | A * | 5/2000 | Sesena et al. ............... | 451/384 |
| 7,150,672 | B2 | 12/2006 | Mizuno | |
| 7,369,238 | B2 * | 5/2008 | Wagner et al. .............. | 356/399 |

FOREIGN PATENT DOCUMENTS

| | | |
|---|---|---|
| EP | 0 727 279 A1 | 8/1996 |
| EP | 0 876 874 A2 | 11/1998 |
| EP | 1 739 472 A1 | 1/2007 |
| EP | 1 839 810 A1 | 10/2007 |
| GB | 2 055 642 A | 3/1981 |
| JP | A 10-132502 | 5/1998 |
| JP | A 2002-283202 | 10/2002 |
| JP | A 2002-292547 | 10/2002 |
| JP | A 2005-279827 | 10/2005 |
| JP | A 2005-288630 | 10/2005 |
| WO | WO 2005/093495 A2 | 10/2005 |
| WO | WO 2005/096074 A1 | 10/2005 |

* cited by examiner

*Primary Examiner*—Robert Rose
(74) *Attorney, Agent, or Firm*—Oliff & Berridge, PLC

(57) ABSTRACT

A cup attaching apparatus for attaching a cup to an eyeglass lens, comprises: a lens mount on which the lens is to be mounted; at least three support pins provided on the lens mount to support the lens when a rear refractive surface of the lens is brought in contact with the support pins; a holding unit adapted to hold the support pins so that a supporting plane defined by the support pins is inclinable; a lens clamp for clamping the lens in cooperation with the lens mount when the lens is mounted on the lens mount; at least three presser pins provided on the lens clamp to clamp the lens when a front refractive surface of the lens is brought in contact with the presser pins; and a locking unit adapted to keep the supporting plane defined by the support pins in a substantially horizontal position when the lens is not clamped between the lens mount and the lens clamp.

8 Claims, 14 Drawing Sheets

FIG. 3
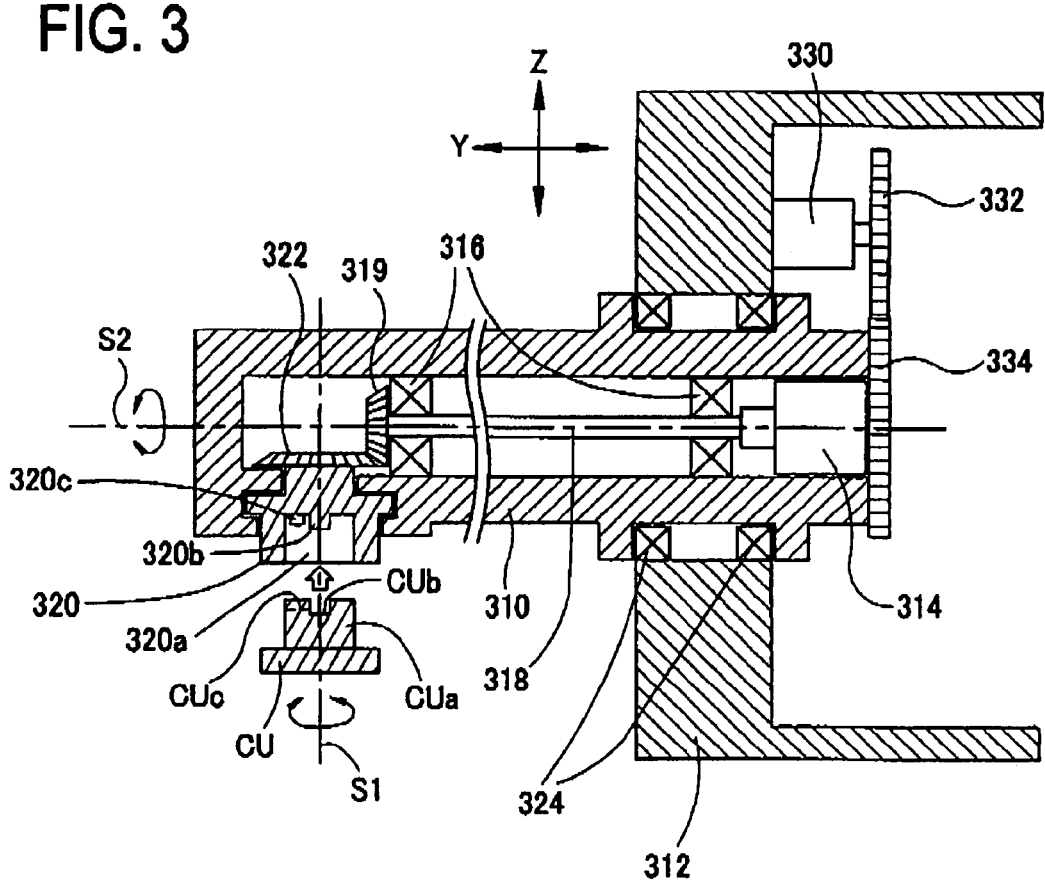
FIG. 4A
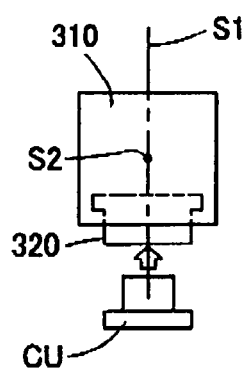
FIG. 4B
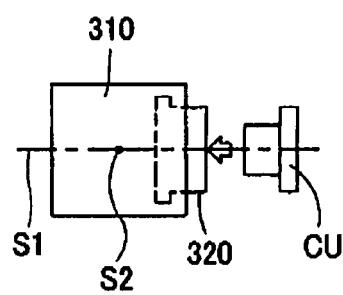
FIG. 4C
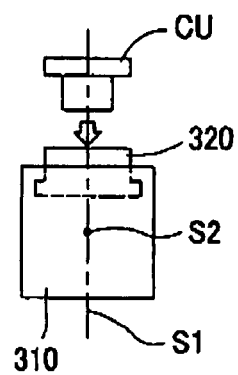
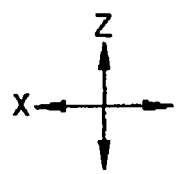
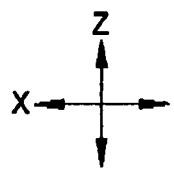
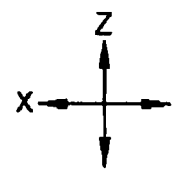

CUP ATTACHING APPARATUS

BACKGROUND OF THE INVENTION

1. Field of the Invention

The present invention relates to a cup attaching apparatus for attaching a cup, used for fixing an eyeglass lens to an eyeglass lens processing apparatus, to the lens.

2. Description of Related Art

There is a cup attaching apparatus called a blocker for attaching a cup, used for fixing an eyeglass lens to an eyeglass lens processing apparatus, to the lens. This cup attaching apparatus comprises a blocking arm provided with a cup holder in the vicinity of a distal end of the arm, the holder being used to hold the cup, and a lens mount (a lens support) on which the lens is to be mounted. When the lens is mounted on the mount, the cup is mounted (fitted) in the holder, and the arm is moved downward, the cup is attached to a front refractive surface of the lens.

Such attaching apparatus is commonly arranged to support a rear refractive surface of the lens with at least three support pins fixedly provided on the mount. A supporting plane defined by the support pins is horizontal and therefore the lens can be supported stably. Thus, even after an operator moves his/her hand off the lens, the cup can be attached to the front refractive surface of the lens.

Meanwhile, in the case where the cup is to be attached to the lens having the rear refractive surface different in shape from the front refractive surface, such as a prism lens and an astigmatic lens (a toric lens), the following problem may arise. When the rear refractive surface of the lens is supported by the support pins fixed with the supporting plane being held in the horizontal position, the front refractive surface of the lens tends to incline, which is likely to cause errors in positioning accuracy in attaching the cup. To avoid such problems, a cup attaching apparatus having a mechanism arranged to simultaneously move the support pins up and down (e.g., WECO CENTERING SYSTEM by WECO OPTICAL MACHINERY, German) has also been proposed.

However, if the supporting plane is allowed to incline by the vertical movement of the support pins, the supported lens is likely to drop off the support pins unless the lens is pressed from above.

BRIEF SUMMARY OF THE INVENTION

The present invention has been made in view of the above circumstances and has an object to provide a cup attaching apparatus capable of attaching a cup to a lens with accuracy and efficiency.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a cup attaching apparatus for attaching a cup to an eyeglass lens, comprising: a lens mount on which the lens is to be mounted; at least three support pins provided on the lens mount to support the lens when a rear refractive surface of the lens is brought in contact with the support pins; a holding unit adapted to hold the support pins so that a supporting plane defined by the support pins is inclineable; a lens clamp for clamping the lens in cooperation with the lens mount when the lens is mounted on the lens mount; at least three presser pins provided on the lens clamp to clamp the lens when a front refractive surface of the lens is brought in contact with the presser pins; and a locking unit adapted to keep the supporting plane defined by the support pins in a substantially horizontal position when the lens is not clamped between the lens mount and the lens clamp.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 3 is a sectional view showing a schematic configuration of a rotating mechanism for a cup holder and a rotating mechanism for a blocking arm;

FIGS. 4A, 4B, and 4C are views showing changing of orientations of the cup holder;

DETAILED DESCRIPTION OF THE PREFERRED EMBODIMENTS

A detailed description of a preferred embodiment of the present invention will now be given referring to the accompanying drawings.

<Overall Configuration>

Figure 1:
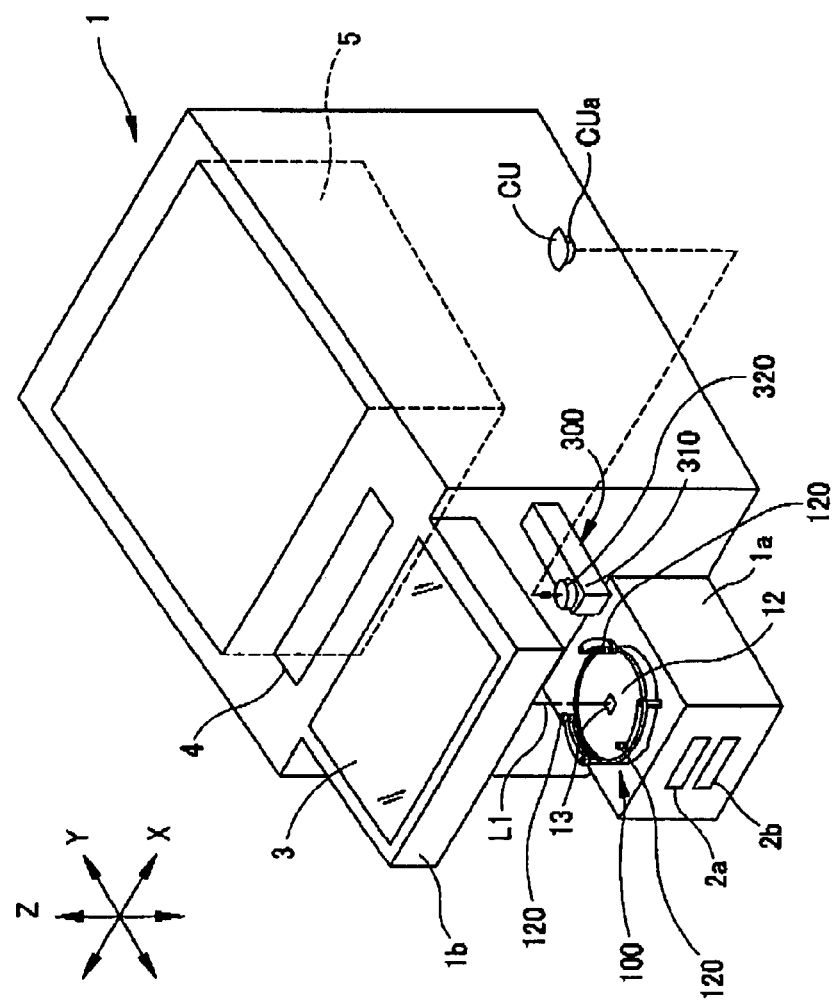
FIG. 1 is a schematic external view of a cup attaching apparatus of a preferred embodiment of the present invention.
Figure 2A:
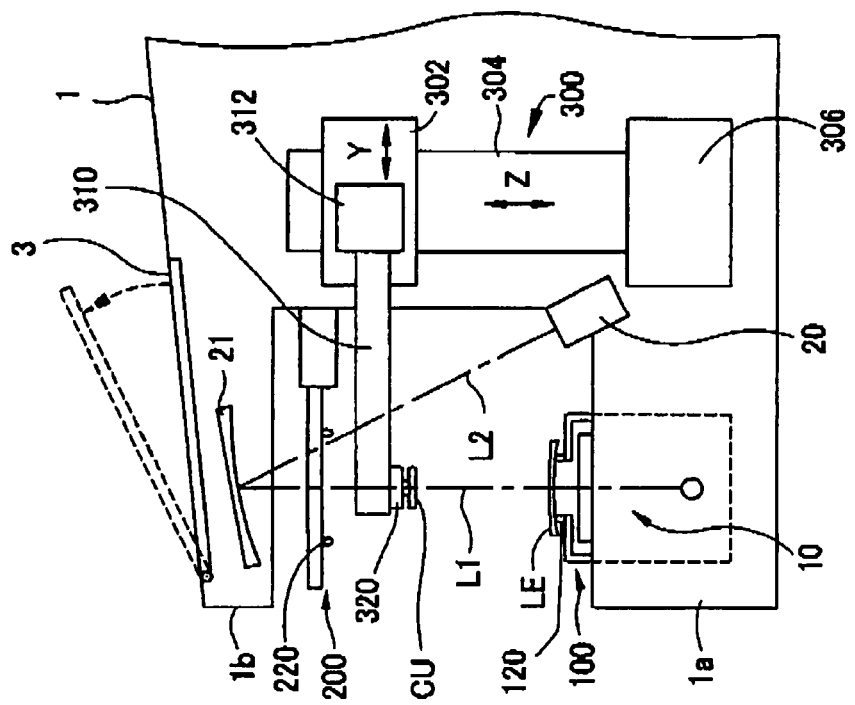
FIGS. 2A and 2B are schematic configuration views of the attaching apparatus.
Figure 2B:
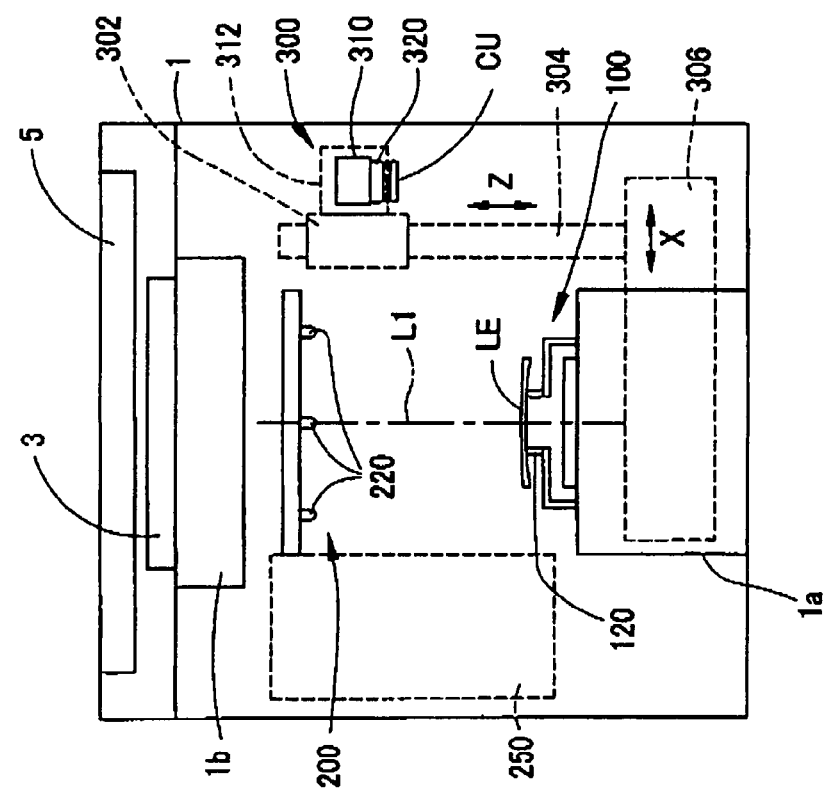

FIG. 1 is a schematic perspective view of a cup attaching apparatus 1 of the present embodiment. FIGS. 2A and 2B are schematic configuration views of the attaching apparatus 1; FIG. 2A is a front view and FIG. 2B is a side view.

In an upper portion of the attaching apparatus 1, an eyeglass frame measuring device 5 is placed (built) and a switch panel (an input part) 4 for the measuring device 5 is placed. In an upper front portion of the attaching apparatus 1, forming a canopy part 1b, a display (a display and input part) 3 of a touch screen type is placed. The display 3 is movable to change the orientation of a screen according to the posture of an operator or the like (see FIG. 2B). On a lower front portion of the attaching apparatus 1 forming a base part 1a, a lens mount (a lens support) 100 having three support pins 120 is placed. Above the lens mount 100, a lens clamp 200 having three presser pins 220 is placed. The lens clamp 200 is movable up and down by a moving unit 250.

On a right portion of the attaching apparatus 1 seen from the front, a blocking unit (a cup attaching unit) 300 for attaching a cup CU to a front refractive surface of an eyeglass lens LE is placed. The blocking unit 300 includes a blocking arm 310 including a cup holder 320 disposed at the vicinity of a distal end thereof, in which the cup CU is to be mounted (fitted).

On the front of the base part 1a, a switch 2a for activating the moving unit 250 and a switch 2b for activating the blocking unit 300 are arranged.

The base part 1a internally contains an illumination optical system 10 for illuminating the lens LE with diffused illumination light. The optical system 10 has an optical axis L1 that passes almost the center of the lens mount 100. The illumination light from the illumination optical system 10 is reflected by a concave mirror 21 placed inside the canopy part 1b. A light receiving optical system 20 for receiving the illumination light reflected by the mirror 21 is placed in a root portion of the base part 1a so that an optical axis L2 of the optical system 20 forms a predetermined angle with respect to the optical axis L1.

<Configuration of Blocking Unit>

The configuration of the blocking unit 300 will be explained referring to FIGS. 2 through 6. The arm 310 which rotatably holds the holder 320 is rotatably held by an arm holding base 312. The holding base 312 is held by a moving unit 302 in such a manner as to be movable backward and forward (in a Y-axis direction). Further, the moving unit 302 is held by a moving unit 304 in such a manner as to be movable upward and downward (in a Z-axis direction). Further, the moving unit 304 is held by a moving unit 306 in such a manner as to be movable rightward and leftward (in an X-axis direction). Each of the moving units 302, 304, and 306 is constituted of a well known moving mechanism including a motor, a sliding mechanism, etc.

FIG. 3 is a sectional view showing a schematic configuration of a rotating mechanism of the holder 320 and a rotating mechanism of the arm 310. The holder 320 is placed near the distal end of the arm 310 in such a manner as to be rotatable about a central axis S1. The arm 310 internally contains a motor 314 whose rotating shaft is coupled to a rear end of a shaft 318 supported by a bearing 316 in such a manner as to be rotatable about a central axis S2. A bevel gear 319 is attached to a front end of the shaft 318 and in mesh with a bevel gear 322 attached to a rear end of the holder 320. Such mechanism causes the holder 320 to rotate about the central axis S1 relative to the arm 310 in conjunction with rotation of the motor 314.

As well known, a base portion CUa of the cup CU is formed with a linear recess CUb and a small circular recess CUc. A hole 320a of the holder 320 in which the base portion CUa is to be fitted is formed with a linear protrusion 320b engageable in the recess CUb and a small circular protrusion 320c engageable in the recess CUc. This makes it possible to control the orientation of the cup CU.

The arm 310 is held by the holding base 312 through a bearing 324 in such a manner as to be rotatable about the central axis S2. The holding base 312 internally contains a motor 330 whose rotating shaft is attached with a spur gear 332 meshing with a spur gear 334 attached to a rear end of the arm 310. Such mechanism causes the arm 310 to rotate about the central axis S2 relative to the holding base 312 in conjunction with rotation of the motor 330. Accordingly, the orientation of the holder 320 can be changed to any one of a downward orientation (see FIGS. 3 and 4A), a sideways orientation (see FIG. 4B), an upward orientation (see FIG. 4C), and others.

Figure 5A:
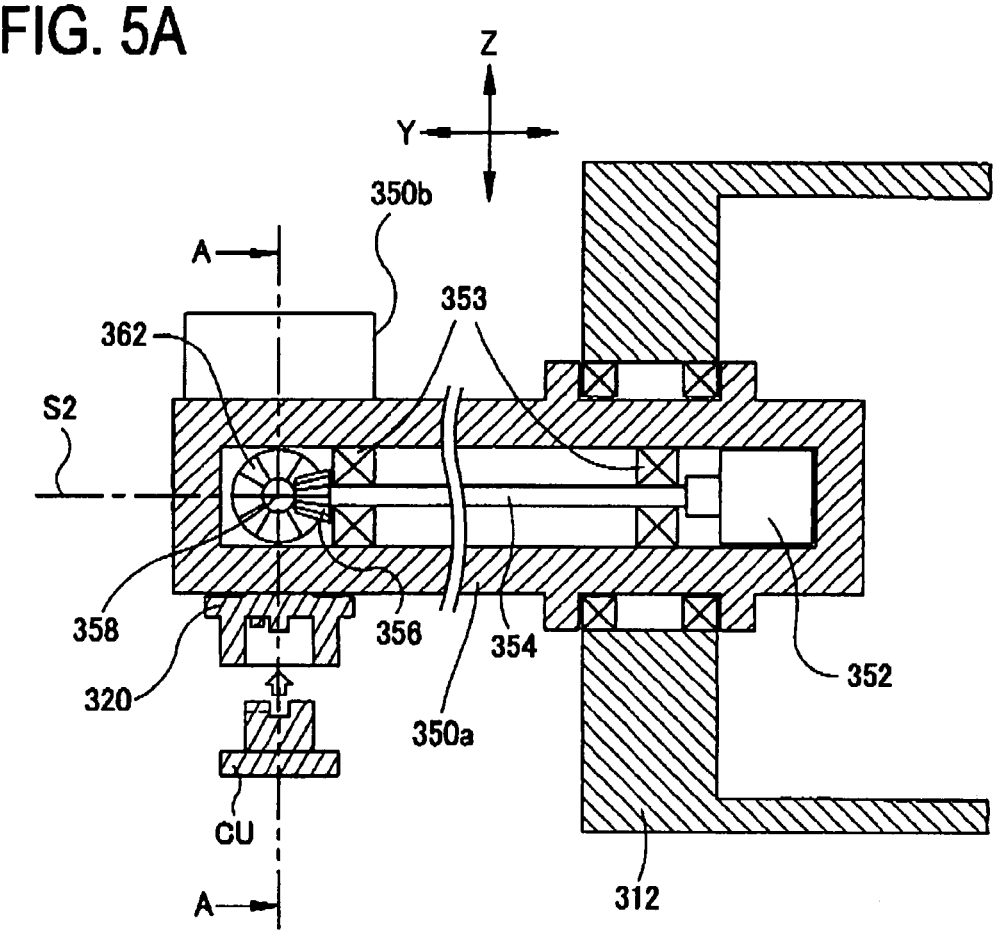
FIGS. 5A and 5B are sectional views showing a schematic configuration of a modified form of the rotating mechanism for the cup holder and the rotating mechanism for the blocking arm.
Figure 5B:
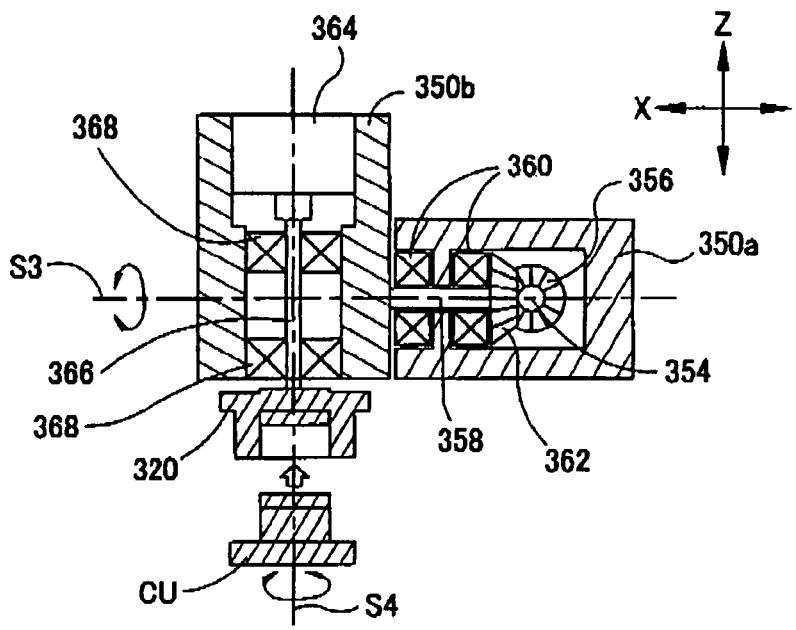
Figure 6A:
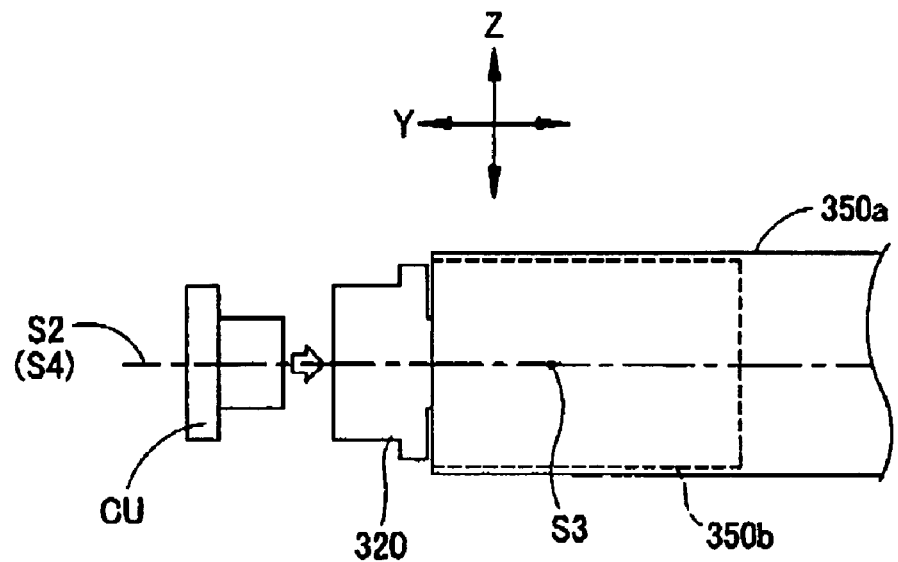
FIGS. 6A and 6B are views showing changing of the orientations of the cup holder.
Figure 6B:
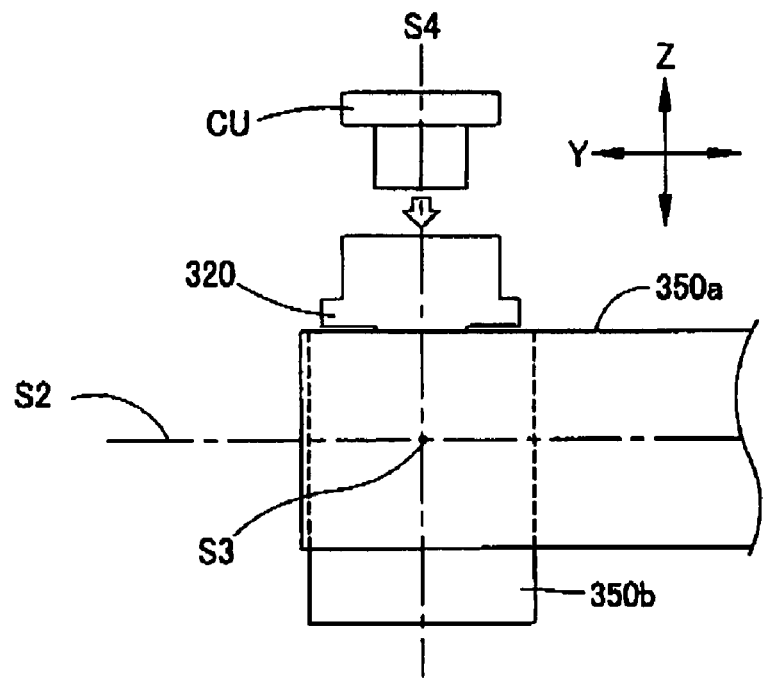

It should be noted that changing of the orientation of the holder 320 is not always effected by rotation of the arm 810 about the central axis S2. For instance, it may be effected by rotation of the arm 310 about an axis perpendicular to the central axis S2. FIGS. 6A and 5B are sectional views showing a schematic configuration of a modified form of the rotating mechanism for the holder 320 and the rotating mechanism for the arm 310; FIG. 5A is a sectional side view and FIG. 5B is a sectional view (a sectional front view) taken along a line A-A in FIG. 5A. The arm 310 includes a first arm 350a and a second arm 350b. The first arm 350a is held by the holding base 312. The second arm 350b is placed near a distal end of the first arm 350a in such a manner as to be rotatable about a central axis S3 perpendicular to the central axis S2. The first arm 350a contains a motor 352 whose rotating shaft is coupled to a rear end of a shaft 354 supported by a bearing 353 in such a manner as to be rotatable about the central axis S2. A bevel gear 356 is attached to a front end of the shaft 354 and in mesh with a bevel gear 362 attached to a shaft 358 that is fixed to an outer surface of the second arm 350b and is supported by a bearing 360 in such a manner as to be rotatable about the central axis S3. Such mechanism causes the second arm 350b to rotate about the central axis S3 relative to the first arm 350a in conjunction with rotation of the motor 352. Accordingly, the orientation of the holder 320 can be changed to any one of the downward orientation (see FIGS. 6A and 6A), a frontward orientation (see FIG. 6A), the upward orientation (see FIG. 6B), and others.

The holder 320 is held near a distal end of the second arm 350b in such a manner as to be rotatable about a central axis S4 perpendicular to the central axis S3. The second arm 350b contains a motor 364 whose rotating shaft is coupled to a rear end of a shaft 366 supported by a bearing 368 in such a manner as to be rotatable about the central axis S4. A front end of the shaft 366 is coupled to a rear end of the holder 320. Such mechanism causes the holder 320 to rotate about the central axis S4 relative to the second arm 350b in conjunction with rotation of the motor 364.

It should be noted that the arm rotating mechanism in FIG. 3 and the arm rotating mechanism in FIG. 5 may be combined. In the configuration in FIG. 5, specifically, the first arm 350a may be adapted to be rotatable about the central axis S2 relative to the holding base 312.

<Configuration of Lens Mount>

Figure 7:
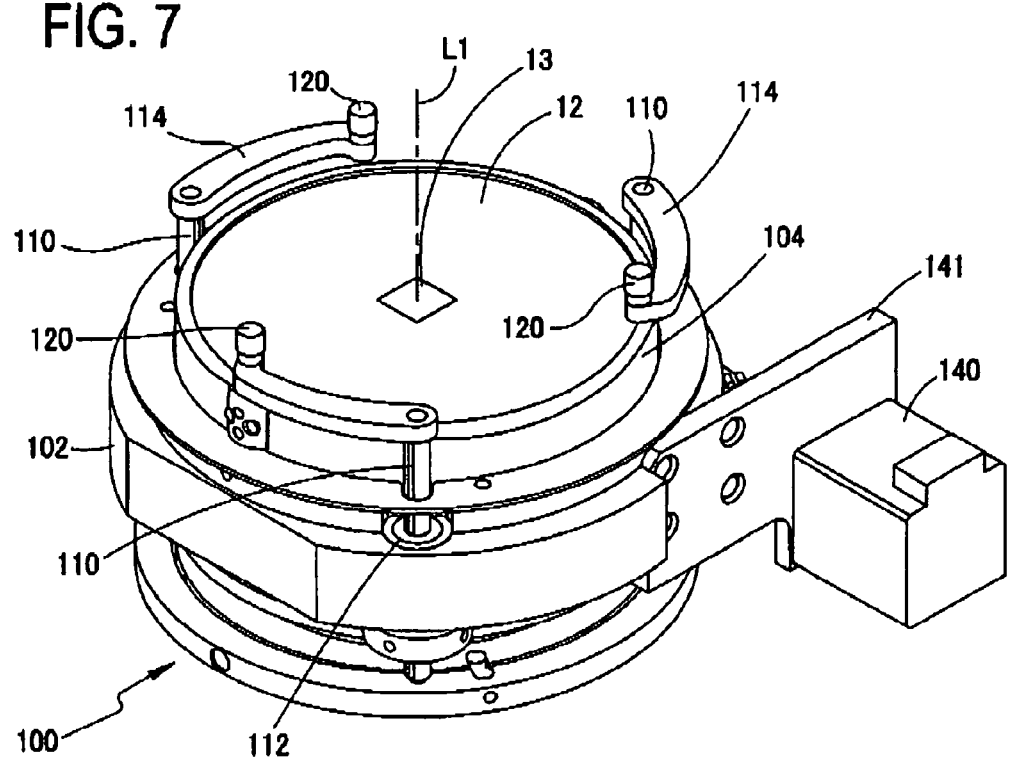
FIG. 7 is a schematic external view of a lens mount.
Figure 8:
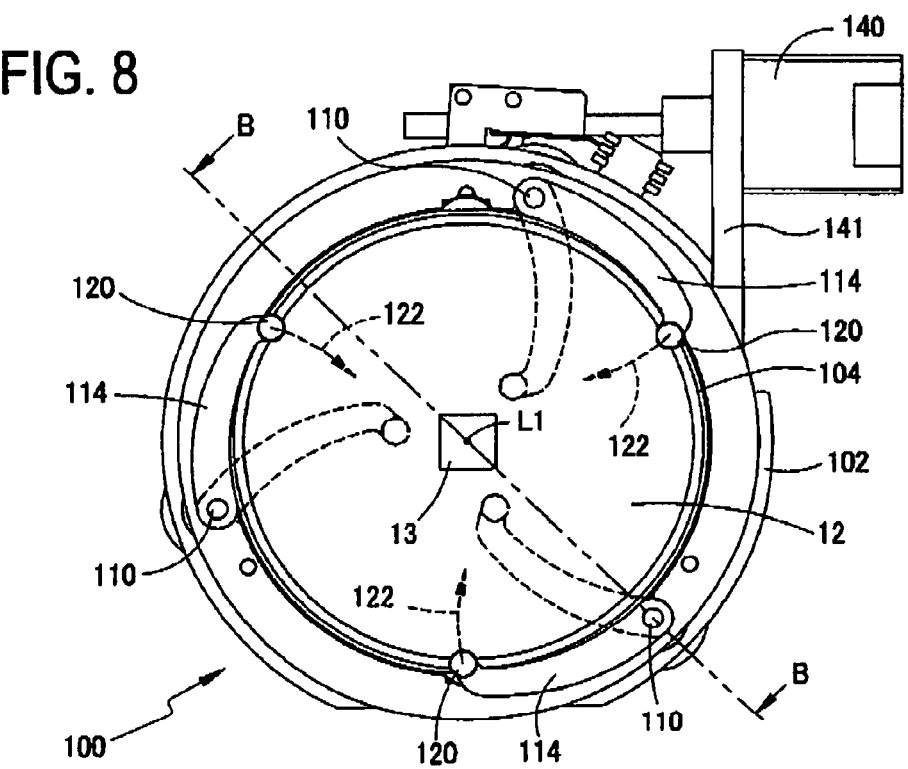
FIG. 8 is a top view of the lens mount.
Figure 9:
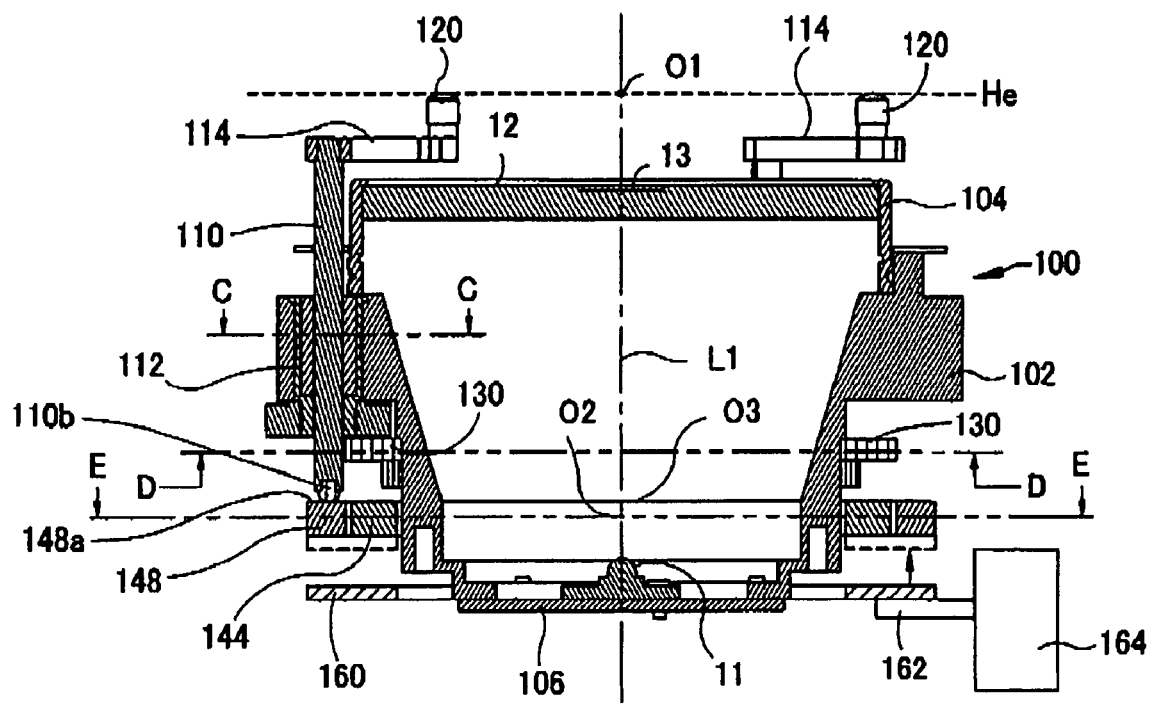
FIG. 9 is a partly sectional view taken along a line B-B in FIG. 8.

The configuration of the lens mount 100 will be explained referring to FIGS. 7 through 12. FIG. 7 is a schematic perspective view of the lens mount 100. FIG. 8 is a top view of the lens mount 100. FIG. 9 is a sectional view (a sectional side view) taken along a line B-B in FIG. 8.

A ring member 104 is placed on the top of a cylindrical mount base 102. In an upper inside of the ring member 104, a diffusing plate 12, which can also be used as a lens table, is fitted. A light source 11 of the illumination optical system 10 is placed on the center of a bottom plate 106 placed under the mount base 102.

In the periphery of the mount base 102, three ball splines 112 each holding a spline shaft 110 in a manner to permit vertical movement of the spline shaft 110 are arranged. Three ball splines 112 are arranged at an equal distance from and circumferentially spaced at equally intervals about the central axis L1 (an axis coinciding with the optical axis L1 of the illumination optical system 10). In other words, three spline shafts 110 are arranged at an equal distance from and circumferentially spaced at equally intervals about the central axis L1. Each ball spline 112 is held in the mount base 102 in such a manner as to be rotatable about the central axis of the spline shaft 110. An arm 114 is attached to an upper end of each spline shaft 110 and provided at its distal end with the support pin 120. To be concrete, three support pins 120 are arranged at an equal distance from and circumferentially spaced at equally intervals about the central axis L1.

Figure 10:
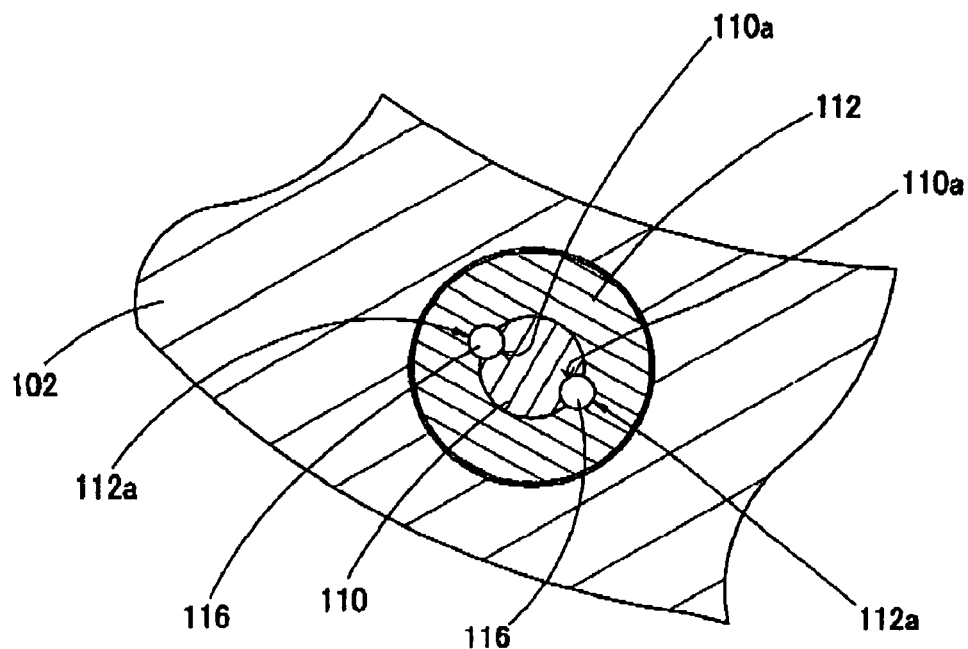
FIG. 10 is a sectional view taken along a line C-C in FIG. 9.

FIG. 10 is a partly sectional view taken along a line C-C in FIG. 9. Each spline shaft 110 is formed with two semicircular grooves 110a extending along the central axis of the spline shaft 110. Each ball spline 112 is also formed with two semicircular grooves 112a facing the grooves 110a. Between the groove 110a and the groove 112a, a ball 116 is interposed. Such mechanism causes the spline shaft 110 to move in the direction of its central axis (in the Z-axis direction) relative to the ball spline 112, and further permits the spline shaft 110 together with the ball spline 112 to rotate relative to the mount base 102.

Figure 11:
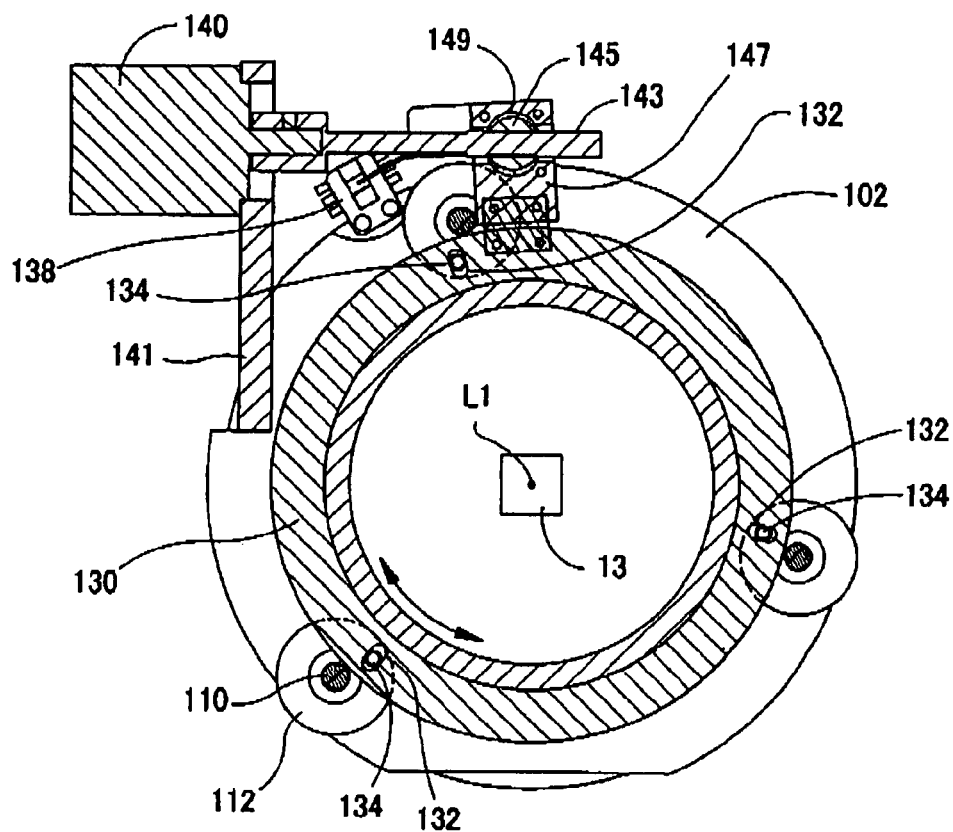
FIG. 11 is a sectional view taken along a line D-D in FIG. 9.

FIG. 11 is a sectional view taken along a line D-D in FIG. 9. Under each ball spline 112, a ring member 130 is held on the periphery of the mount base 102 in such a manner as to be rotatable about the central axis L1. The ring member 130 is formed with long holes 132 each radially extending in correspondence with the position of each ball spline 112. Each ball spline 112 is provided with a pin 134 standing in the position deviated from the central axis of the spline shaft 110 and engaging in the hole 132. The pin 134 is arranged in the position deviated from the rotating center of the ball spline 112 (the central axis of the spline shaft 110) and, accordingly, when the ring member 130 is rotated about the central axis L1, the pin 134 is guided in the hole 132, thereby rotating the ball spline 112 about the central axis of the spline shaft 110, simultaneously rotating the spline shaft 110. This permits the support pin 120 provided in the distal end of each arm 114 to move radially inwardly from a standby position (see FIGS. 7 and 8) as indicated by an arrow 122. In other words, as the distances of the support pins 120 from the central axis L1 are changed simultaneously, the intervals between the support pins 120 are changed.

The mount base 102 is provided with a motor 140 for rotating the ring member 130, through a plate 141. A rotating shaft of the motor 140 is coupled to a feed screw 143 on which a nut 145 is threadably engaged. On the other hand, the ring member 130 is provided with an engagement member 147 having a hole 149 in which the nut 145 is engaged. By such mechanism, when the screw 143 is rotated by rotation of the motor 140, the nut 145 is moved in the central axial direction of the screw 143, thereby making the ring member 130 rotate about the central axis L1. A sensor 138 is placed to detect an initial position of rotation of the ring member 130. It should be noted that the ring member 130 may be rotated by hand.

Figure 12:
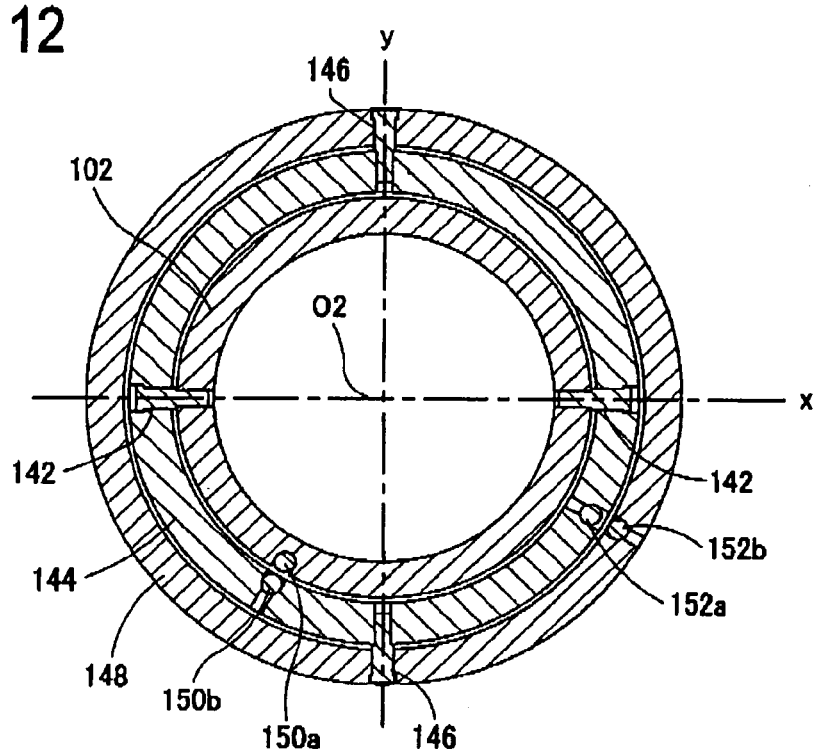
FIG. 12 is a sectional view taken along a line E-E in FIG. 9.

FIG. 12 is a sectional view taken along a line E-E in FIG. 9 and also an explanatory view for showing an inclination mechanism for a supporting plane (level) He defined by the support pins 120. An x-axis inclining ring member 144 is placed around the mount base 102 and a y-axis inclining ring member 148 is placed around the ring member 144. The ring member 144 is connected to the mount base 102 with two connecting shafts 142 located on the x-axis in FIG. 12 so that the ring member 144 can be rotated about the x-axis. The ring member 148 is connected to the ring member 144 with two connecting shafts 146 located on the y-axis in FIG. 12, perpendicular to the x-axis, so that the ring member 148 can be rotated about the y-axis. This permits the ring member 148 to incline two-dimensionally about a point O2 on the central axis L1 and accordingly an upper surface 148a of the ring member 148 to incline two-dimensionally about a point O3 on the central axis L1. As shown in FIG. 9, on the upper surface 148a of the ring member 148, three lower ends 110b of the spline shafts 110 are placed. The spline shafts 110 are moved up and down as the ring member 148 inclines two-dimensionally, so that the supporting plane He defined by the support pins 120 is inclined two-dimensionally about a point O1 on the central axis L1 passing that supporting plane He. This inclination of the supporting plane He is restricted in a position where an undersurface of each of the arms 114 comes into contact with the edge of the ring member 104. A permissible inclination range is set at about 6°, for example.

Columnar magnets 150a and 150b are embedded to face each other in an outer surface of the mount base 102 and an inner surface of the ring member 144 respectively. Similarly, columnar magnets 152a and 152b are embedded to face each other in an outer surface of the ring member 144 and an inner surface of the ring member 148 respectively. When the lens clamp 200 (the presser pins 220) is not in contact with the front refractive surface of the lens LE, the ring member 148 (the upper surface 148a) is held in a horizontal position by magnetic forces of the magnets 150a and 150b that attract each other and magnetic forces of the magnets 152a and 152b that attract each other, thereby horizontally keeping the supporting plane He. In other words, the magnets 150a, 150b, 152a, and 152b constitute means for horizontally keeping the supporting plane He defined by the support pins 120 and serve as an urging member that applies an urging force to the support pins 120 to make the supporting plane He horizontal. The magnetic force (the urging force) of the magnet 150a and others serving as the urging member is determined to be strong enough to reliably keep the supporting plane He in the horizontal position against a load on the support pins 120 when the lens LE is mounted on the support pins 120 and enough to allow the support pins 120 and the spline shafts 110 and others to move up and down under a load on the lens LE when the lens LE is pressed by the presser pins 220.

It should be noted that the means for returning and keeping the supporting plane He in the horizontal position may be a resilient member such as a plate spring serving as the urging member, instead of using the magnet 150a and others.

AB means for locking the supporting plane He defined by the support pins 120 in the horizontal position, a locking ring member 160 is placed below the ring members 144 and 148 in such a manner as to be movable up and down. An upper surface of the ring member 160 is able to come into contact with respective lower surfaces of the ring members 144 and 148. The ring member 160 is fixed to an arm 162 which can be moved up and down by a moving unit 164. When the ring member 160 is moved up into contact with the ring members 144 and 148 by operation of the moving unit 164, the ring members 144 and 148 are inhibited from inclining and hence the supporting plane He defined by the support pins 120 is also inhibited from inclining (locked in the horizontal position). When the ring member 160 is moved downward to come out of contact with the ring members 144 and 148, the ring members 144 and 148 are permitted to incline and hence the supporting plane He is also allowed to incline. The means for locking the supporting plane He in the horizontal position may be configured such that the ring member 148, the ring member 144, and the mount base 102 are locked to each other with pins or the like inserted through them.

The means for horizontally keeping the supporting plane He by the magnets 160a and others and the means for locking the supporting plane He in the horizontal position with the ring member 160 and others may be applied to a lens mount (a lens support) provided with support pins spaced at constant intervals.

<Configuration of Lens Clamp>

Figure 13:
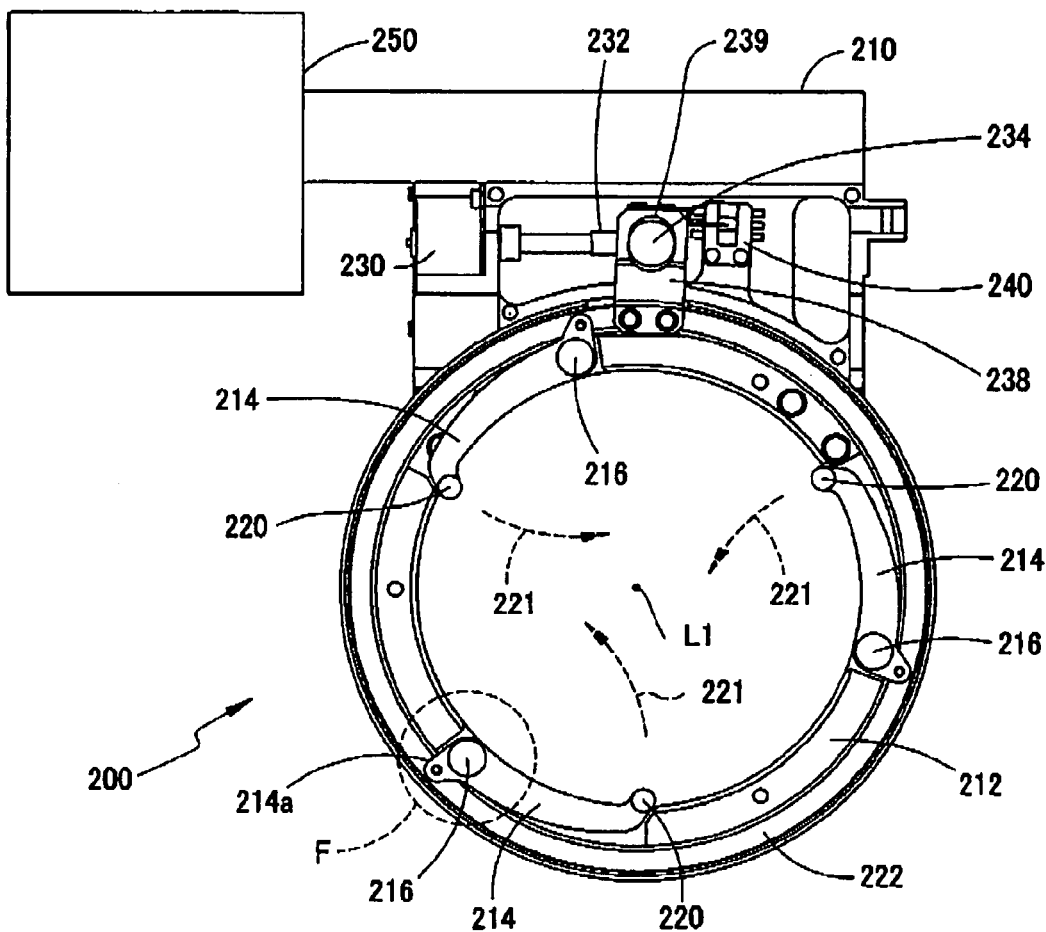
FIG. 13 is a bottom view of a lens clamp.
Figure 14:
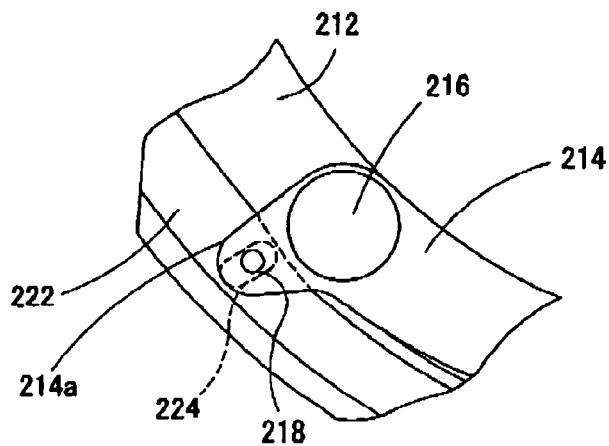
FIG. 14 is an enlarged view of a portion F in FIG. 13.

The configuration of the lens clamp 200 will be explained referring to FIGS. 13 and 14. FIG. 13 is a bottom view of the lens clamp 200 and FIG. 14 is an enlarged view of a part F in FIG. 13. At the back of the attaching apparatus 1, a clamp base 210 is placed to be movable in the Y-axis direction by the moving unit 250. Fixed on the clamp base 210 is a ring member 212 centered on the central axis L1. The ring member 212 includes three arms 214 provided at respective distal ends with the presser pins 220, each arm 214 being rotatable about a fixed shaft 216. Around the ring member 212, a ring member 222 is placed to be rotatable about the central axis L1. It should be noted that three presser pins 220 are arranged at an equal distance from and circumferentially spaced at equally intervals about the central axis L1. The presser pins 220 are positioned with respective end faces being flush with one another. In other words, the presser pins 220 are provided in the lens clamp 200 so that a pressing plane defined by the presser pins 220 is in a substantially horizontal position.

Each arm 214 includes a base plate 214a extending over the ring member 222. The ring member 222 is formed with long holes 224 each radially extending. On the other hand, each base plate 214a is provided with a pin 218 engaging in the hole 224. By such mechanism, when the ring member 222 is rotated, each arm 214 is rotated about each shaft 216, thereby moving each presser pin 220 attached to the distal end of each arm 214 from a standby position (see FIG. 13) as indicated by an arrow 221. In other words, as the distances of the presser pins 220 from the central axis L1 are changed simultaneously, the intervals between the presser pins 220 are changed.

The clamp base 210 is provided with a motor 230 for rotating the ring member 222. A rotating shaft of the motor 230 is coupled to a feed screw 232 on which a nut 234 is threadably engaged. On the other hand, the ring member 222 is provided with an engagement member 238 having a hole 239 in which the nut 234 is engaged. By such mechanism, when the screw 232 is rotated by rotation of the motor 230, the nut 234 is moved in the central axial direction of the screw 232, thereby making the ring member 222 rotate about the central axis L1. A sensor 240 is placed to detect an initial position of rotation of the ring member 222.

Figure 15:
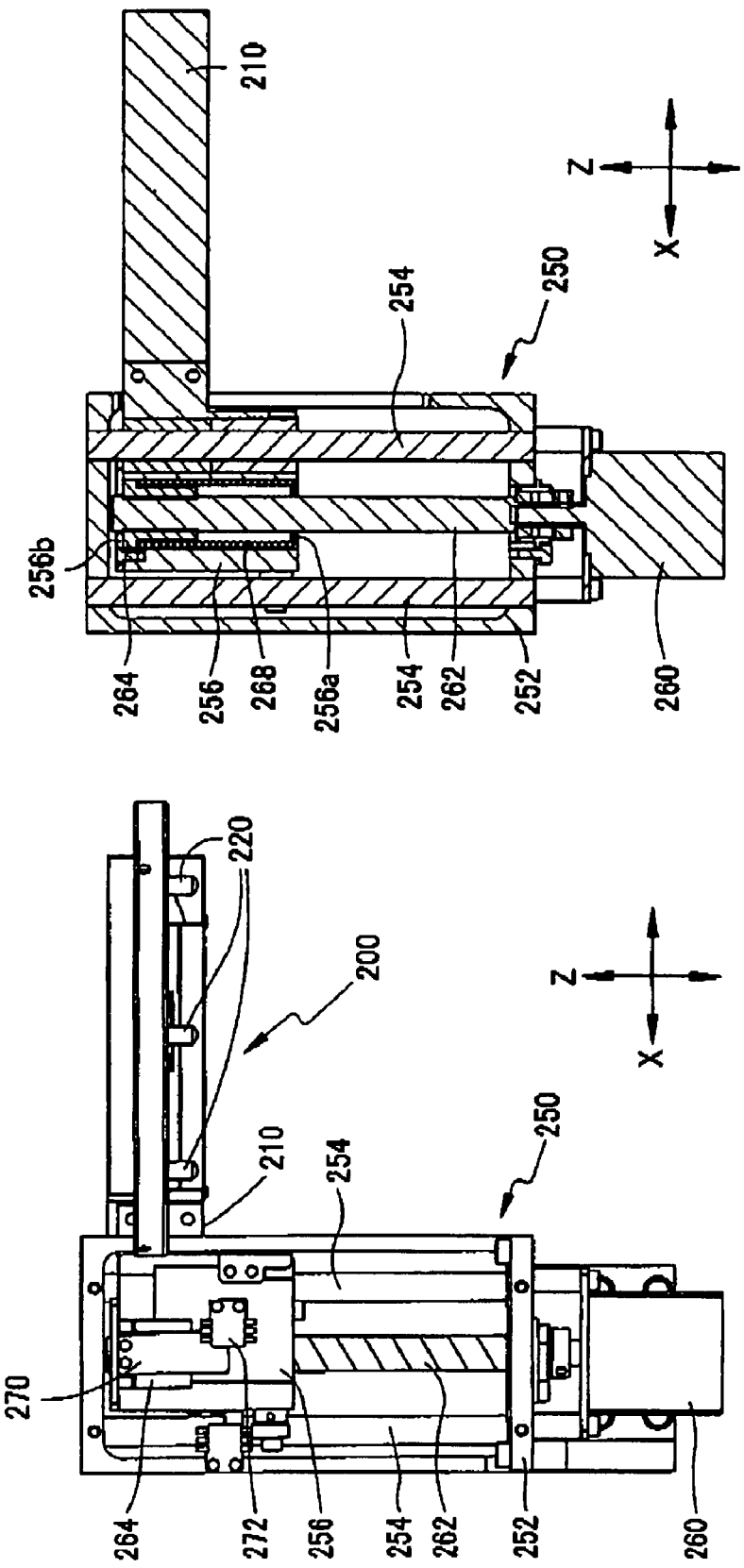
FIGS. 15A and 15B are schematic configuration views of a moving unit for the lens clamp.

The configuration of the moving unit 250 will be explained referring to FIGS. 15A and 15B. FIG. 15A is a front view of the moving unit 250 and FIG. 15B is a sectional view of the same viewed along a plane passing through each center of two guide shafts 254 and a feed screw 262. On a unit base 252, the guide shafts 254 are mounted extending in the Y-axis direction. A moving block 256 is supported on the guide shafts 254 in such a manner as to movable in the Y-axis direction. The moving block 256 is fixed to the clamp base 210. Below the unit base 252, a motor 260 is placed with its rotating shaft being coupled to the feed screw 262. On the feed screw 262, a nut 264 is threadably engaged in a manner so as to be non-rotatable relative to the moving block 256 but movable in the Y-axis direction. A coil spring 268 is interposed between a lower end of the nut 264 and a bottom portion 256a of the moving block 256. A plate 256b placed at the top of the moving block 256 restricts upward travel of the nut 264.

When rotation of the motor 260 produces a driving force to move the nut 264 downward, the nut 264 moves the moving block 256 downward through the spring 268, and thus the clamp base 210 fixed to the moving block 256 is also moved down. The nut 264 is provided with a light shielding plate 270. The moving block 256 is provided with a sensor 272 for detecting the position of the light shielding plate 270. As the clamp base 210 is moved downward, the presser pins 220 are brought into contact with the front refractive surface of the lens LE supported on the support pins 120. In this state, the clamp base 210 and the moving block 256 are no longer able to further move downward, and only the nut 264 is allowed to further move downward against an urging force of the spring 268. As the nut 264 is further moved downward, the light shielding plate 270 is also moved downward and becomes detected by the sensor 272. By a detection signal of the sensor 272, it is detected that the presser pins 220 are placed in contact with the front refractive surface of the lens LE. At the time of attachment of the cup CU, the motor 260 is driven from the time of detection of the sensor 272 to further move the nut 264 downward to apply an increased pressing force of the lens clamp 200 by the urging force of the spring 268 to the lens LE. After the attachment of the cup CU, when the motor 260 is driven to move the nut 264 upward, the clamp base 210 as well as the moving block 256 is moved upward.

<Configurations of Optical system and Control System>

Figure 16:
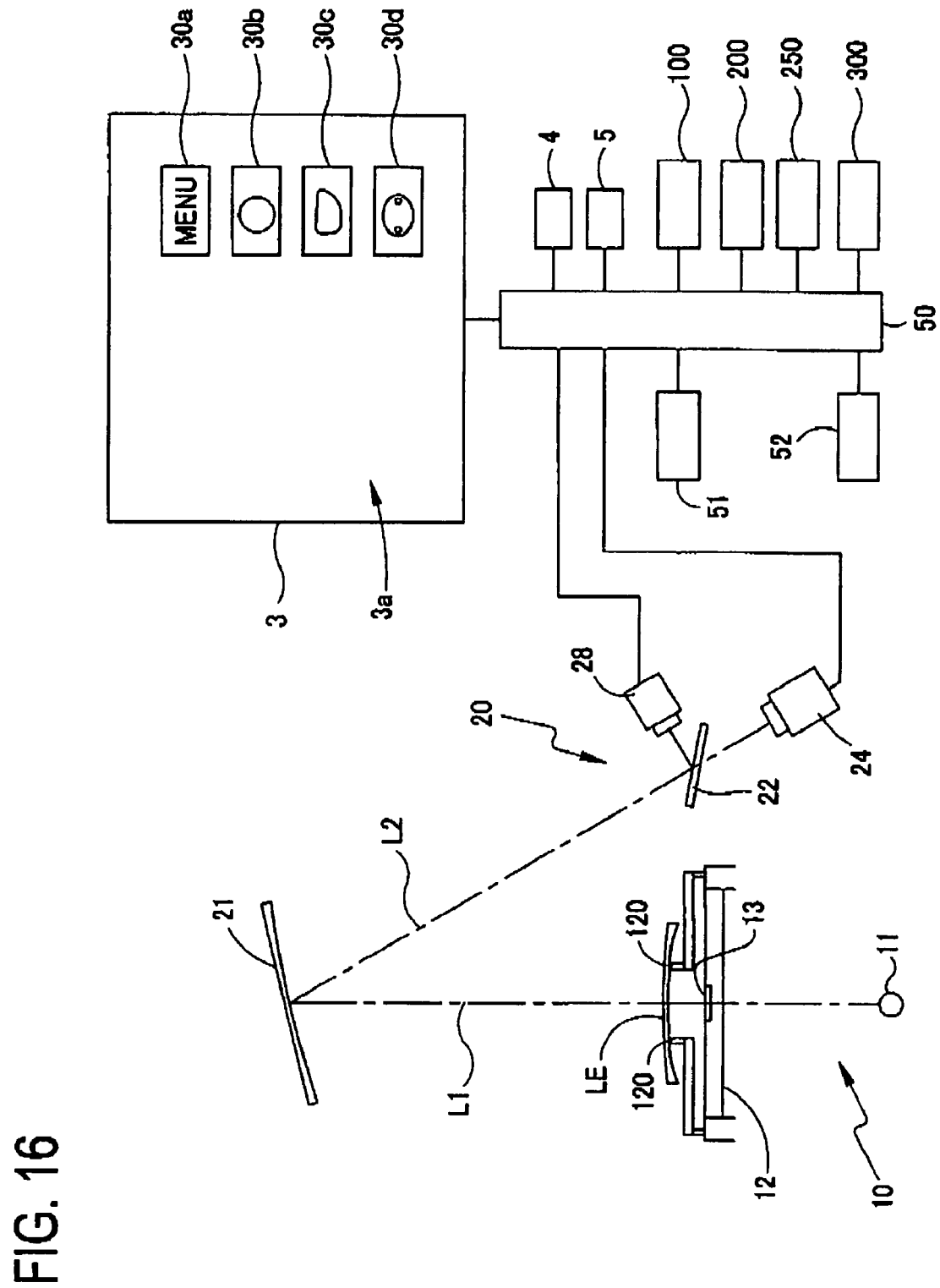
FIG. 16 is a schematic configuration diagram of an illumination optical system and a light receiving optical system of the attaching apparatus and a schematic block diagram of a control system of the attaching apparatus.

FIG. 16 is a schematic configuration diagram of the illumination optical system 10 and the light receiving optical system 20 and a schematic block diagram of a control system of the attaching apparatus 1. The illumination optical system 10 includes the light source 11 such as an LED which emits white light and the diffusing plate 12 having a diffusing plane larger than the lens LE. Formed on a surface of the diffusing plate 12 is an index part 13 including measurement indexes arranged in a regular pattern centered on the central axis L1. The measurement indexes of the index part 13 are for example a plurality of dot indexes spaced at equally intervals. The light receiving optical system 20 includes a half mirror 22 located on the optical axis L2 in a reflecting direction of the concave mirror 21, a CCD camera (an imaging unit) 24 located on the optical axis L2 on a transmission side of the half mirror 22, and a CCD camera (an imaging unit) 28 located on the optical axis L2 on a reflection side of the half mirror 22. An image of the lens LE is captured by the camera 28 and displayed on the display 3.

The cameras 24 and 28 are connected to an arithmetic control section 50. When the lens LE having refractive power is mounted on the lens mount 100 (the support pins 120), this arithmetic control section 50 obtains an optical center and the direction of a cylinder axis of the lens LE, etc. based on images of the measurement indexes captured by the camera1 24, and further obtains a shape (a contour) of the lens LE, etc. based on an image of the lens LE captured by the camera 28.

A brief explanation is made on a method for calculating the optical center and the direction of the cylinder axis of the lens LE based the measurement index images. For instance, in the case where the plurality of dot indexes spaced at equally intervals are the measurement indexes, changes in the positions of the measurement index images formed when the lens LE is mounted on the lens mount 100 are detected in comparison with the positions of the measurement index images formed when the lens LE is not mounted on the lens mount 100. The center of changes in the positions is obtained as the optical center. In the case where the lens LE has cylinder power, the direction of changes in the positions of the measurement index images is detected. The direction of changes in the positions is obtained as the cylinder axis direction. As this detecting method, a similar method to that disclosed in JP-A-2002-292547 may be adopted.

Connected to the arithmetic control section 50 are the moving units 302, 304, and 306 of the blocking unit 300 and the motors 314 and 330 (or the motors 362 and 364). Also connected to the arithmetic control section 50 are the motor 140, the sensor 138, and the moving unit 164 of the lens mount 100, and also the motor 230, the sensor 240, the moving unit 250 (the motor 260), and the sensor 272 of the lens clamp 200.

The operations of the apparatus having the above configuration will be described below.

<Mounting of Cup>

Figure 17:
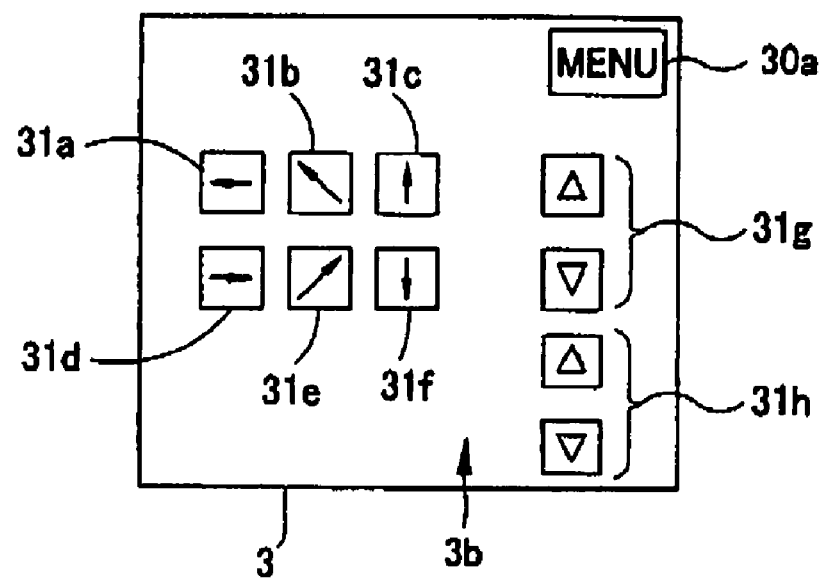
FIG. 17 is a view showing a setting screen for the orientation of the cup holder.

The following explanation is made first on how to change the orientation of the holder 320 placed in a standby position. The standby position of the arm 310 when the cup CU is to be mounted is the right portion of the apparatus 1 seen from the front, as shown in FIGS. 1 and 2. When a menu button 30*a* appearing on an initial screen 3*a* (see FIG. 16) of the display 3 is pressed (touched), an orientation setting screen 3*b* (see FIG. 17) for the orientation of the holder 320 appears. When one of buttons 31*a* to 31*f* on the setting screen 3*b* is pressed, the orientation of the holder 320 is specified (chosen). In the present embodiment, the button 31*a* is pressed to specify "leftward orientation", seen from the front of the apparatus 1, the button 31*b* is pressed to specify "obliquely left-upward orientation", the button 31*c* is pressed to specify "upward orientation", the button 31*d* is pressed to specify "rightward orientation", the button 31*e* is pressed to specify "obliquely right-upward orientation", and the button 31*f* is pressed to specify "downward orientation".

When any of the buttons 31*a* to 31*f* is pressed, the arithmetic control section 50 activates the motor 830 to rotate the arm 310 to bring the holder 320 into the specified orientation. In the case where an operator conducts mounting work while standing, for example, the holder 320 is preferably placed in the upward orientation to facilitate the mounting of the cup CU to the holder 320.

The orientation of the holder 320 relative to the arm 310 can be adjusted with buttons 31*g*. Specifically, while an up button "Δ" of the buttons 31*g* is being pressed, the arithmetic control section 50 activates the motor 314 to rotate the holder 320 to the left (counterclockwise). While a down button "∇" of the buttons 31*g* is being pressed, the arithmetic control section 50 activates the motor 314 to rotate the holder 320 to the right (clockwise).

The height of the holder 320 (the arm 310) can also be adjusted with buttons 31*h*. Specifically, while an up button "Δ" or a down button "∇" of the buttons 31*h* is being pressed, the arithmetic control section 50 activates the moving unit 304 to change the height of the arm 310.

After completion of the setting of the orientation and height of the holder 320, the menu button 30*a* is pressed, closing the setting screen 3*b*, and set data on the orientation and height of the holder 320 are stored in a memory 51. Accordingly, the orientation and height of the holder 320 in the arm 310 placed in the standby position before and after the cup CU is attached thereto is adjusted to the specified orientation and height (see FIGS. 1 and 2).

It should be noted that the case where the arm rotating mechanism of FIGS. 5A and 5B is adopted, it may be adapted to specify (choose) the orientation of the holder 320 from among "frontward orientation", "obliquely front-upward orientation", "upward orientation", "obliquely front-downward orientation", "downward orientation", and the like. The orientation of the holder 320 by the rotation of the holder 320 and the height of the holder 320 (the arm 310) may also be made adjustable.

<Attaching of Cup to Unprocessed Lens>

Attaching of the cup CU to an unprocessed lens LE is explained below. When a mode selecting button 30*b* appearing on the initial screen 3*a* of the display 3 is pressed, an unprocessed lens blocking mode is established and an input screen for inputting target lens shape data and layout data appears on the display 3. The target lens shape data on an eyeglass frame obtained by the measuring apparatus 5 is stored in the memory 51 at the press of a data transfer button not shown. A target lens shape graphic based on the input target lens shape data is displayed on the display 3. Then, with buttons, not shown in the figure, appearing on the display 3, the layout data such as a FPD (frame pupillary distance) of the eyeglass frame, a PD (pupillary distance) of a person who wears the eyeglass, and the height of the optical center of the lens relative to the geometric center of the target lens shape, the type of the lens (a monofocal lens, a progressive multifocal lens, etc.), and the type of the eyeglass frame (with a rim, with no rim, etc.) are input. If the lens LE has cylinder power, data on an angle of the cylinder axis is further input.

Figure 18A:
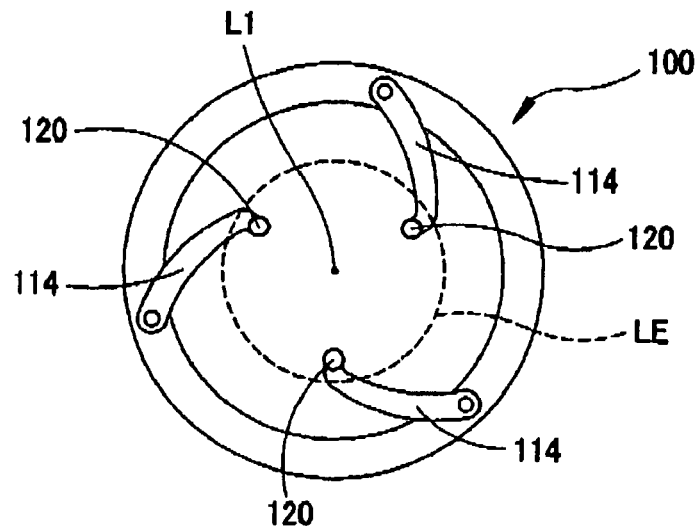
FIGS. 18A, 18B, and 18C are views showing positions of support pins in a unprocessed lens blocking mode, a processed lens blocking mode, and a shape measuring mode.

When the unprocessed lens blocking mode is specified (selected), the arithmetic control section 50 activates the motor 140 of the lens mount 100 to rotate the arms 114 from the standby position, thereby moving the support pins 120 to predetermined positions suitable for mounting the unprocessed lens LE. For instance, the support pins 120 are moved to positions on a circle which is 40 mm in diameter and centered on the central axis L1 (see FIG. 18A). The positions (the intervals) of the support pins 120 can be changed on a setting screen, not shown in the figure, which will appear at the press of the menu button 30*a*. In this mode, the ring member 160 is put in a lower standby position, so that the supporting plane He defined by the support pins 120 is allowed to incline.

When the unprocessed lens blocking mode is specified (selected), the arithmetic control section 50 also activates the motor 230 of the lens clamp 200 to rotate the arm 214 from the standby position, thereby moving the presser pins 220 to predetermined positions. For instance, the presser pins 220 are moved to positions on a circle which is 50 mm in diameter and centered on the central axis L1. The positions (the intervals) of the presser pins 220 can be changed on a setting screen, not shown in the figure, which will appear at the press of the menu button 30*a*.

The supporting plane He defined by the support pins 120 is kept horizontally by the horizontality keeping means such as the magnet 150*a* and others. Accordingly, the lens LE is stably mounted on the support pins 120.

After the lens LE is mounted on the lens mount 100 (the support pins 120), when the switch 2*a* is pressed, the arithmetic control section 50 activates the moving unit 250 to move the moving block 256 downward, thereby bringing the presser pins 220 into contact with the front refractive surface of the lens LE. When the sensor 272 detects that the presser pins 220 come in contact with the lens LE, the arithmetic control section 50 stops the operation of the motor 260 based on that detection signal. At this stage, the lens LE has been pressed just slightly and hence is so movable on the support pins 120 as to adjust the position thereof.

Even in the case where the lens LE mounted on the support pins 120 is a lens having a rear refractive surface different in shape from the front refractive surface, such as a prism lens and an astigmatic lens (a toric lens), the front refractive surface portion of the lens LE to which the cup CU is to be attached can be held in the substantially horizontal position by the lens mount 100 adapted to allow the supporting plane He defined by the support pins 120 to incline. Thus, the cup CU can be attached to the front refractive surface of the lens LE with accuracy.

When the lens LE is pressed by the lens clamp 200, attaching of the cup CU is started. When the switch 2b is pressed, the arithmetic control section 50 obtains the optical center position of the lens LE based on the measurement index images captured by the camera 24, and accordingly obtains data on the deviation of the optical center relative to the central axis L1 and data on the cylinder axis angle. Based on those data and the layout data with respect to the target lens shape, the attaching position and angle of the cup CU are determined. The arithmetic control section 50 successively activates the blocking unit 300.

In the case where the orientation of the holder 320 has been set to the upward orientation and others, the arithmetic control section 50 activates the motor 330 to rotate the arm 310, 180 degrees, to make an attachment surface of the cup CU face down. Based on the attaching position and angle of the cup CU, thereafter, the arithmetic control section 50 activates the motor 314 to rotate the holder 320 and also activates the moving units 302, 304, and 306 to move the arm 310 downward to attach the cup CU to the front refractive surface of the lens LE.

When the switch 2b is pressed, the arithmetic control section 50 activates the motor 260 of the moving unit 260 to rotate by only an amount corresponding to a fixed number of pulses, thereby moving the nut 264 downward to increase the pressing force to the lens LE by the urging force of the spring 268.

When the attachment of the cup CU to the lens LE is completed, the arm 310 is returned to the standby position again. At this time, the orientation of the holder 320 remains in (returns to) the specified one. After completion of the attachment of the cup CU, the lens clamp 200 is moved up to return to a standby position, thus removing the load on the lens LE. Accordingly, the supporting plane He defined by the support pins 120 is returned to and kept in the horizontal position again by the horizontality keeping means such as the magnet 150a and others.

As the means for horizontally keeping the supporting plane He defined by the support pins 120, the ring member 160 and the moving unit 164 serving as the locking means may be utilized as an alternative to the magnet 150a and others. In other words, the inclination of the supporting plane He defined by the support pins 120 has only to be allowed when the lens LE is pressed by the lens clamp 200 (the presser pins 220). When the presser pins 220 are moved upward, the arithmetic control section 50 activates the moving unit 164 to move the ring member 160 upward, thereby locking the ring member 148 horizontally. When the lens LE is mounted on the support pins 120 and then the switch 2a is pressed, the arithmetic control section 50 causes the pressure pins 220 to move downward and the ring member 160 to move downward in interlocked relation to the downward movement of the pressure pins 220, releasing the locked state of the supporting plane He. After attachment of the cup CU, the arithmetic control section 50 causes the presser pins 220 to move upward and the ring member 160 to move upward in interlocked relation to the upward movement of the presser pins 220, thereby locking the ring member 148 horizontally.

<Attaching of Cup to Processed Lens>

Attaching of the cup CU to a processed cup LE is explained below. When a mode selecting button 30c on the initial screen 3a of the display 3 is pressed, a processed lens blocking mode is established and an input screen for inputting the target lens shape data and the layout data is displayed on the display 3.

Figure 18B:
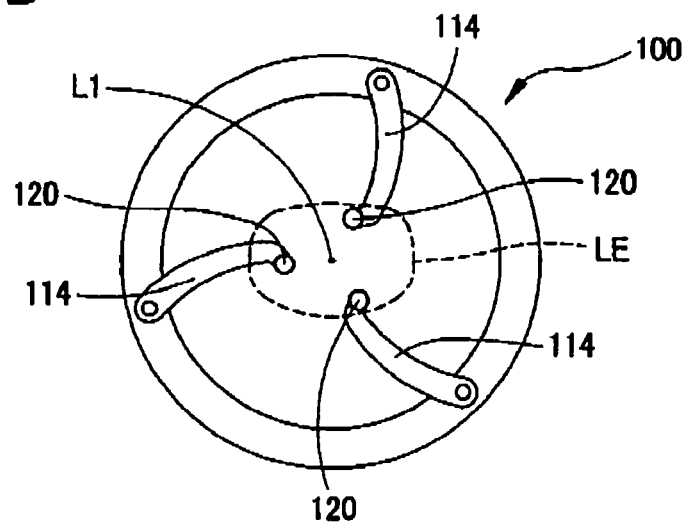

When the processed lens blocking mode is specified (selected), the arithmetic control section 50 activates the motor 140 of the lens mount 100 to rotate the arm 114 from the standby position, moving the support pins 120 to predetermined positions suitable for mounting of the processed lens LE (at narrower intervals than those in the unprocessed lens blocking mode). For instance, the support pins 120 are moved to positions on a circle which is 20 mm in diameter and centered on the central axis L1 (see FIG. 18B). The positions (the intervals) of the support pins 120 can be changed on a setting screen, not shown in the figure, which will appear at the press of the menu button 30a.

In the case of the processed lens LE, which is of a small outer shape, when the lens LE is pressed by the presser pins 220 arranged at narrower intervals, the cup CU is likely to collide with the presser pins 220 at the time of attachment of the cup CU. In the case where the processed lens blocking mode is specified (selected), therefore, the lens clamp 200 is not used. When the processed lens blocking mode is specified (selected), the arithmetic control section 50 controls the activation of the moving unit 164 to move the ring member 160 upward, locking the horizontal position of the supporting plane He defined by the support pins 120.

After the lens LE is mounted on the lens mount 100 (the support pins 120), the cup CU is attached to the lens LE. This attachment of the cup CU to the lens LE is effected in the same manner as the case of the unprocessed lens, and the explanation thereof is not repeated herein.

<Measuring of Outer shape and Setting of Hole of Demo Lens>

Figure 19:
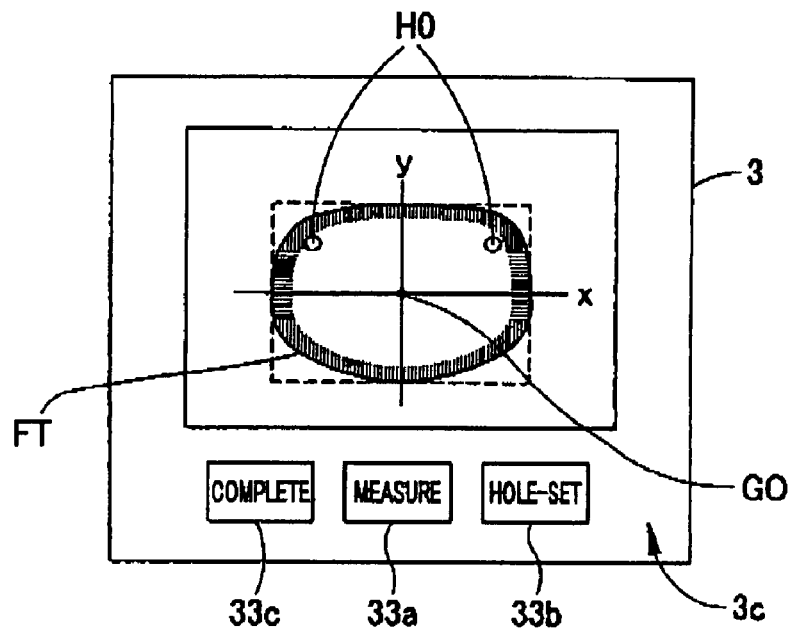
FIG. 19 is a diagram showing a measuring screen for a shape of a demo lens.

An explanation will be made on the setting of a hole position and others by measuring an outer shape (a contour) of a demo lens (including a template) with the frame having no rim. When a mode selecting button 30d on the initial screen 3a of the display 3 is pressed, a lens outer shape measuring mode is established. In this mode, the support pins 120 and the arms 114, if existing within an outer shape measuring area, are likely to interfere with the measurement. Thus, the arithmetic control section 50 causes the support pins 120 to move to the standby positions outside the diffusing plate 12 (outside the measuring area). When the lens outer shape measuring mode is specified (selected), furthermore, a measuring screen 3c (see FIG. 19) appears on the display 3. In the case of measuring the outer shape of the demo lens, the edge of the demo lens is colored with a felt-tip pen or the like to emphasize the lens contour in order to facilitate the measurement.

Figure 18C:
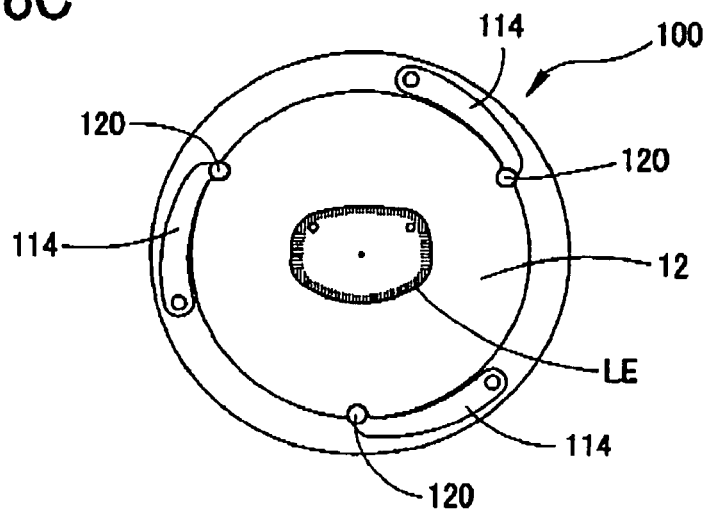

As shown in FIG. 18C, the demo lens LE mounted on the diffusing plate 12 is illuminated with the diffused illumination light of the illumination optical system 10. The image of the lens LE is captured by the camera 28 and displayed on the display 3. At the press of a Measure button 33a on the measuring screen 3c, the measurement of the outer shape and the hole positions based on the obtained image of the lens LE is started. Since a distance and image-magnifying power of an imaging optical system including the camera 28 and others with respect to the diffusing plate 12 are well known in design, the outer shape of the lens LE can be detected by performing image-processing on contrast of the image of the lens LE captured by the camera 28. The arithmetic control section 50 obtains data on the outer shape and data on the hole position of the lens LE by processing the image of the lens LE. When obtains the outer shape data, the arithmetic control section 50 causes an outline FT of the lens LE to appear in red in a superimposed manner on the image of the lens LE displayed on the measuring screen 3c. Further, a geometric center GO of the lens LE is determined based on the outer shape data and a coordinate of the center point of each hole HO relative to the geometric center GO is obtained. It should be noted that the front refractive surface of the lens LE is applied with three dot marks in advance by a lensmeter or the like so that the dot marks represent a horizontal direction of the lens LE which a person will wear the eyeglass. This makes it possible for the operator to position the lens LE so that the three dot marks become parallel with the x-axis while viewing the image of the lens LE displayed on the measuring screen 3c.

Figure 20:
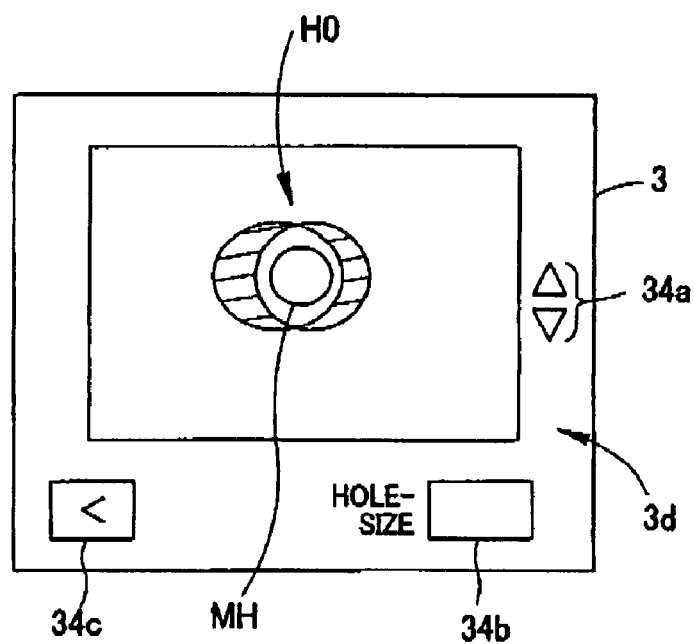
FIG. 20 is a view showing a setting screen for positions of holes and others.

In the case where the position and the size of each hole HO are set in detail, a Hole-set button 33b on the measuring screen 3c is pressed after the hole HO is specified, and thus a setting screen 3d (see FIG. 20) showing the specified hole HO in an enlarged form appears. A hole mark MH is displayed on the hole HO and adjusted while being moved with a stylus pen or the like not shown, thereby determining the position of the hole HO. A hole size button 34a on the setting screen 3d is pressed to variously adjust the size of the hole mark MH to determine the size of the hole HO. The determined size of the hole HO is displayed in a hole size box 34b. When a return button 34c on the setting screen 3d is pressed, the screen is returned to the measuring screen 3c. For terminating the outer shape measuring and the hole setting, a Complete button 33c on the measuring screen 3d is pressed and thus the screen returns to the initial screen 3a. The obtained outer shape data and the hole data are stored in the memory 51. The data stored in the memory 51 can be output to a hole-making device (an eyeglass lens processing apparatus including a hole-making part) connected to an output part 52.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A cup attaching apparatus for attaching a cup to an eyeglass lens, comprising:
   a lens mount on which the lens is to be mounted;
   at least three support pins provided on the lens mount to support the lens when a rear refractive surface of the lens is brought in contact with the support pins;
   a holding unit provided on the lens mount and adapted to hold the support pins so that a supporting plane defined by the support pins is inclineable, the holding unit including a mount base, a first ring member placed on the mount base to be swingable in a first direction, a second ring member placed on the first ring member to be swingable in a second direction perpendicular to the first direction, and shafts each having a distal end provided with each support pin;
   a lens clamp for clamping the lens in cooperation with the lens mount when the lens is mounted on the lens mount;
   at least three presser pins provided on the lens clamp to press the lens when a front refractive surface of the lens is brought in contact with the presser pins;
   a blocking unit including a cup holder and a blocking arm provided with the cup holder, the blocking unit being configured to attach the cup to the lens placed on the lens mount; and
   a locking unit adapted to inhibit the first and second ring members from swinging so as to lock the supporting plane in a substantially horizontal position when the lens is not clamped between the lens mount and the lens clamp and permit the first and second ring members to swing when the lens is clamped between the lens mount and the lens clamp.

2. The cup attaching apparatus according to claim 1, further comprising:
   a control section for controlling driving of the locking unit.

3. The cup attaching apparatus according to claim 2, further comprising a moving unit adapted to move the lens clamp in an up-and-down direction, and
   wherein the control section controls driving of each of the moving unit and the locking unit in interlocking relation.

4. The cup attaching apparatus according to claim 2, further comprising a mode selector for selecting between a first mode for attaching the cup to an unprocessed lens and a second mode for attaching the cup to a processed lens;
   wherein
   the control section controls driving of the locking unit to permit the first and second ring members to swing when the first mode is selected and inhibit the first and second ring members from swinging when the second mode is selected.

5. The cup attaching apparatus according to claim 1, wherein
   the locking unit includes an urging member having an urging force
   insufficient to allow the first and second ring members to swing against a load occurring when the lens supported by the support pins is not pressed by the presser pins but sufficient to allow the first and second ring members to swing against the load occurring when the lens supported by the support pins is pressed by the presser pins.

6. The cup attaching apparatus according to claim 5, wherein the urging member is a magnet.

7. The cup attaching apparatus according to claim 1, wherein the presser pins are provided on the lens clamp so that a pressing plane defined by the presser pins is substantially horizontal.

8. The cup attaching apparatus according to claim 1, further comprising:
   a first moving unit adapted to move the blocking arm in an up-and-down direction;
   a second moving unit adapted to move the lens clamp in the up-and-down direction; and
   a control section adapted to control driving of each of the first and second moving units.

* * * * *